(12) United States Patent
Ryu

(10) Patent No.: US 7,172,771 B2
(45) Date of Patent: Feb. 6, 2007

(54) METHODS FOR PREPARING RED GINSENG AND PUFFED SNACK ENRICHED WITH RED GINSENG USING EXTRUSION PROCESS

(76) Inventor: Gi-Hyung Ryu, Dept. of Food Science and Technology College of Industrial Science, Kongju National University, Yesan, Chungnam (KR) 340-802

( * ) Notice: Subject to any disclaimer, the term of this patent is extended or adjusted under 35 U.S.C. 154(b) by 31 days.

(21) Appl. No.: 10/895,293

(22) Filed: Jul. 21, 2004

(65) Prior Publication Data

US 2005/0019428 A1    Jan. 27, 2005

(30) Foreign Application Priority Data

Jul. 22, 2003   (KR)   .................. 10-2003-0050142
Jul. 1, 2004    (KR)   .................. 10-2004-0050953

(51) Int. Cl.
    *A61K 36/00*   (2006.01)
(52) U.S. Cl. ................ 424/728; 426/448; 426/498
(58) Field of Classification Search ............ 424/728; 426/448, 498
    See application file for complete search history.

(56) References Cited

U.S. PATENT DOCUMENTS 6,899,902 B1 *  5/2005  Hwang .................. 424/728

FOREIGN PATENT DOCUMENTS

DE    100 08 293 A1 *   2/2000

OTHER PUBLICATIONS

* Sang-Dal Kim et al., "Effects of Processing Methods on the Quality of Ginseng Leaf Tea", Korean J. Food Sci. Technol., vol. 13, No. 4 (1981), pp. 267-272. English abstract only.
* Dae-Cherl Ha et al., "Drying Rate and Physicochemical Characteristics of Dried Ginseng Root at Different Temperature", J. Korean Soc. Food Sci. Nutr., 33(4), (2004), pp. 741-746. English abstract only.
* Gi-Hyung Ryu, "Treatment of Biji by Extrustion-Cooking and Its Utilization", Korea Soybean Digest 12(2) (1995), pp. 43-48.

(Continued)

*Primary Examiner*—Christopher Tate
*Assistant Examiner*—S. B. McCormick-Ewoldt
(74) *Attorney, Agent, or Firm*—Buchanan Ingersoll & Rooney PC

(57) ABSTRACT

The present invention relates to methods for preparing red ginseng and puffed snack enriched with red ginseng, from raw ginseng or white ginseng, using an extrusion process. The red ginseng and red ginseng powder prepared according to the present invention can be produced at larger amounts within a shorter time period than those of the conventional method for preparing red ginseng. In addition, since the red ginseng and red ginseng powder of the present invention need not to be subjected to an additional powdering step, they may be directly used as a raw material of secondary processed red ginseng products. Furthermore, as the directly puffed snack and indirectly puffed pellet prepared according to the method of present invention contain a high concentration of red ginseng, they may be used for light meals and cocktail appetizers while providing a health promotion effect.

9 Claims, 3 Drawing Sheets

OTHER PUBLICATIONS

* Judson M. Harper, "Extrusion of Foods", vol. 1, published by CRC Press, Inc., Boca Raton, Florida, Chapter 1, pp. 1-15 (1981).

* C. Mercier et al., "Extrusion Cooking", published by American Association of Cereal Chemists, Inc., Chapter 1, pp. 1-6 (1989).

* cited by examiner

FIG. 3

← red ginseng powder

← white ginseng powder

← maltol reference standard

← example No. 12

← example No. 11

← example No. 10

← example No. 9

← example No. 8

← example No. 7

← example No. 6

← example No. 5

← example No. 4

← example No. 3

← example No. 2

← example No. 1

METHODS FOR PREPARING RED GINSENG AND PUFFED SNACK ENRICHED WITH RED GINSENG USING EXTRUSION PROCESS

FIELD OF THE INVENTION

The present invention relates to methods for preparing red ginseng and puffed snack enriched with red ginseng, using an extrusion process.

BACKGROUND OF THE INVENTION

Ginseng has been widely used from ancient times as the most typical nutritional tonic in some countries including Korea, China and other countries. Recently, the results of many studies on its components and pharmacological actions have been reported. The reported pharmacological actions of ginseng include central nervous system depression and excitation, protein and nucleic acid biosynthesis promotion, hematosis, liver function recovery, blood pressure lowering and elevation, arteriosclerosis prevention, blood glucose increase, anti-fatigue and anti-stress actions. In addition, ginseng was recently reported to have an AIDS virus growth inhibitory action, an anti-dioxin action and a sexual function improvement effect.

Generally, ginseng is used in the following three forms: raw ginseng (fresh ginseng) remaining intact without any processing after its harvest; white ginseng obtained by drying raw ginseng at ambient temperature; and red ginseng obtained by steaming and drying raw ginseng. Particularly, ginseng is used in the form of red ginseng because red ginseng shoes a higher pharmacological activity than that of raw ginseng or white ginseng.

Red ginseng is prepared according to the steps of: washing raw ginseng; steaming the washed ginseng at 90–100° C.; drying the steamed ginseng to a moisture content of 35–40 wt %; storing and aging the dried ginseng; drying the aged ginseng again to a moisture content of about 16 wt %; and trimming the dried ginseng. Compared with the raw ginseng, the red ginseng prepared as such shows an improvement in storage stability, a change in its components, and browning.

Particularly, during the step of steaming raw ginseng in the preparing process of red ginseng, the components of raw ginseng are chemically changed. For this reason, new components which are not found in raw ginseng or white ginseng are detected in red ginseng, and the amounts of other components which are originally contained in the raw ginseng also increased. Important components produced during the preparing process of red ginseng include saponin compounds, and non-saponin compounds such as polyacetylenes, acidic polysaccharides and amino acids. Of the non-saponin compounds, panaxytriol is a characteristic component found only in red ginseng. It is reported that red ginseng has higher saponin contents, about eight times higher acidic polysaccharide contents and about 25 times higher amino acid contents than those of white ginseng prepared from the same amount of raw ginseng.

Meanwhile, an extrusion process is an efficient and economic process as compared with other processes, because its unit operations, such as mixing, crushing, heating, molding and drying, are performed within a short time period. Since a material within an extruder undergoes not only shear force by the rotation of a screw but also pressure by the adjustment of a die exit, the extrusion process is a continuous process which involves physical force at high temperature and high pressure, particularly when applied to a heating process (Harper, *Extrusion Cooking*, pp 1–16, 1989).

From the 1930s, the extrusion process started to be regularly applied in industry as a solution in labor-intensive fields. A field in which the extrusion process had been first applied as a continuous process is a polymer plastic molding field, and recently, the extrusion process is applied in various industrial fields including food, feed, biological and medical products.

Since pasta was produced by a continuous process using a single-screw extruder in the middle 1930s, the extrusion process started to be systemically applied in the food industry (Harper, *Extrusion of Foods*, pp. 1–6, 1981). Application examples of the extrusion process in the food field include the puffed corn snack products, the pregellatinized starch, the texturization of vegetable protein, the pretreatment of fat extract, the sterilization, the conversion of polymeric biomaterials, and the conversion of residues in the preparation of bean-curds into intermediate products (RYU Gi-Hyung, *Korean Society of soybean study* 12(2): 43–48, 1995). However, there has been no case where the extrusion process was used for the processing of ginseng, particularly the preparation of red ginseng.

SUMMARY OF THE INVENTION

In the course of conducting continued studies to develop a method allowing the mass production of red ginseng, the present inventors have found that not only red ginseng which has useful components and excellent efficacy but also puffed food enriched with red ginseng can be prepared by the extrusion process, thereby completing the present invention.

An object of the present invention is to provide a method for preparing red ginseng using the extrusion process.

Another object of the present invention is to provide a method for preparing puffed food enriched with red ginseng using the extrusion process.

DETAILED DESCRIPTION OF THE PREFERRED EMBODIMENTS

In order to achieve the above object, the present invention provides a method for preparing red ginseng which comprises the steps of drying raw ginseng and extruding the dried raw ginseng in an extruder.

In the method for preparing the red ginseng according to the present invention, the drying step is preferably to reduce the moisture content to a range of 5–40 wt %. Moreover, the method according to the present invention may additionally comprise the step of crushing the raw ginseng into pieces, preferably before the drying step.

In the method for preparing the red ginseng according to the present invention, the die exit temperature of the extruder preferably is 70–150° C., and the screw rotational speed of the extruder is preferably 100–400 rpm.

In order to achieve another object, the present invention provides a method for preparing puffed food enriched with red ginseng, the method comprising the steps of: mixing raw ginseng with grain powder; drying the mixture; and extruding the dried mixture in an extruder with injecting compressed gas.

In the method for preparing the puffed food enriched with red ginseng according to the present invention, the grain powder may be selected from the group consisting of starch, unpolished rice powder, rice powder, wheat powder, corn powder, glutinous rice powder, barley powder and a mixture thereof. Moreover, the drying step is preferably to reduce the moisture content to a range of 5–40 wt %. Furthermore, the method may additionally comprise the step of crushing the raw ginseng into pieces, preferably before the drying step.

In the method for preparing the puffed food enriched with red ginseng according to the present invention, the die exit temperature of the extruder is preferably 70–180° C., and the screw rotational speed of the extruder is preferably 100–400 rpm. The compressed gas injection may be performed by injecting $CO_2$ at a pressure of 0.1–10 MPa. Furthermore, the method may additionally comprise the steps of drying and cutting the extrudate.

In the method for preparing the puffed food enriched with red ginseng according to the present invention, the puffed food may be a directly puffed snack extruded at a die exit temperature of 105–180° C. Also, the puffed food may be an indirectly puffed pellet extruded at a die exit temperature of 70–105° C.

Hereinafter, the present invention will be described in detail.

In one aspect, the present invention provides a method for preparing red ginseng using an extrusion process.

Each step of the method for preparing red ginseng according to the present invention will now be described.

Step 1: Pre-drying of Fresh Ginseng

In order to prepare red ginseng according to the present invention, raw ginseng is dried.

In the present invention, all kinds of raw ginseng plants can be used, and their producing districts are not critical to the present invention.

For the easy introduction into an extruder, the easy movement in the extruder and the generation of mechanical energy by friction, the moisture content of raw ginseng, which generally has a moisture content of 75–80 wt %, needs to be adjusted to less than 40 wt %, and preferably 5–40 wt %. Measurement of the moisture content of raw ginseng may be carried out using an automatic moisture meter.

White ginseng generally having a moisture content of less than 10 wt % and prepared by the drying of raw ginseng, can be used in the method of present invention without passing through the pre-drying step.

Before drying, raw ginseng can be washed with water to remove foreign materials or contaminants from its surface, and then water remaining on its surface can be removed.

Although raw ginseng itself can be dried, it is preferably crushed into pieces having the desired size, and more preferably a size similar to that of a rice grain, in order to shorten the drying time.

A method which can be used in this pre-drying step of raw ginseng includes, but is not limited to, ambient temperature drying, hot air drying and freeze drying. In order to maximize the amount of ginsenosides contained in raw ginseng after drying, the hot air drying method is preferable as compared with the freeze-drying method (see Table 2).

In one test example of the present invention, not only the rate of decrease in moisture content according to a change in drying temperature but also the physicochemical properties of the dried raw ginseng were analyzed in order to optimize the hot air drying temperature. The drying rates were different between 80° C. and 100° C., but not different greatly between 100° C. and 120° C. Furthermore, there was no significant difference of ginsenoside contents between 100° C. and 120° C. However, the exudation rate of browning substances showed a tendency to increase as the drying temperature increases (see Table 2). Such results suggest that it is preferred that raw ginseng is dried at a temperature of 70–120° C., particularly 100° C.

Step 2: Extrusion

The raw ginseng having been dried in said pre-drying step is fed into an extruder and extruded in the extruder.

If the raw ginseng has been crushed into pieces before the pre-drying step, the raw ginseng itself can be fed into the extruder. In the case of white ginseng and the raw ginseng having been dried without crushing, they can preferably be crushed before being fed into the extruder.

Generally, extruders are classified into a screw type and a non-screw type. The screw-type extruders are classified into a single-screw extruder and a multiple-screw extruder. A twin-screw extruder showing a uniform and high extruder output even at low screw rotational rate and allowing stable extrusion is mainly used. Generally, the screw-type extruder is consisting of a driving motor unit for rotating a screw; a control unit for controlling the rotational speed of the screw; a screw unit; a body unit surrounding around the screw unit and having an inlet port at one end and an outlet port at the other end; a heating unit for heating the body; a cooling unit for cooling the body and the like.

Although the present invention utilized the screw-type extruder, particularly the twin-screw extruder, the scope of the invention is not limited to this extruder. In one embodiment of the present invention, the screw lent-to-diameter (L/D) ratio of the twin-screw extruder was 25:1, a reverse pitch screw was distributed at a location of L/D 13 in order to increase residual time and shear force, and the diameter of a circular die exit was 2.0 mm.

This extrusion step is preferably performed at a dried raw ginseng-feeding rate of 80–150 g/min, a die exit temperature of 70–150° C. and a screw rotational speed of 100–400 rpm.

Step 3: Drying and Grinding

Although the red ginseng extrudate prepared in the above extrusion step may also be used intact, it is preferably dried to a moisture content of less than 13 wt % in order to improve its storage stability.

A drying method which can be used for drying the extrudate in this step includes, but not limited to, ambient temperature drying, hot air drying and freeze drying. The hot air drying at 100° C. is preferred.

Moreover, although the crushed red ginseng can be used intact, it may also be ground to prepare red ginseng powder. The grinding of the crushed red ginseng in this step is not limited to particular methods, and may be performed using a commercially available grinder.

In one test example of the present invention, the components of the red ginseng prepared according to the method of present invention were compared with those of the red ginseng prepared by the conventional method. The results showed that, in the case of ginsenosides among the components of the red ginseng prepared by the method of present invention, the contents of $R_f$, $R_e$, $R_d$, $R_c$ and $R_{b2}$ were higher than those of the conventional red ginseng, the content of $R_{b1}$ was similar to that of the conventional red ginseng, and the contents of $R_{g1}$, $R_{g2}$ and $R_{g3}$ were lower than those of the conventional red ginseng. Moreover, the total amount of ginsenosides in each of the red ginseng products prepared in examples of the present invention was higher than that of the conventional red ginseng (see Table 4).

Furthermore, the total sugar and reducing sugar content of the red ginseng prepared according to the method of present invention were similar to those of the conventional red ginseng, but its acidic polysaccharide content was somewhat lower than that of the conventional red ginseng (see Table 5). Also, maltol having antioxidant activity, which is a characteristic component of red ginseng and found only in red ginseng but not in raw ginseng, was detected in all the red ginseng products according to the present invention (see FIG. 3).

From the results described above, it could be confirmed that raw ginseng is converted into red ginseng by the method of present invention, and the components of the red ginseng prepared by the method of present invention are generally similar to those of the conventional red ginseng.

In one test example of the present invention, the chromaticity of the red ginseng prepared according to the method of present invention was compared with that of the red ginseng prepared by the conventional method. The results showed that the brightness, yellowness, redness and total color difference of the red ginseng prepared according to the present invention were similar to those of the conventional red ginseng (see Table 6).

In order to test the quality stability of the red ginseng prepared according to the method of present invention, the red ginseng was stored at room temperature, high temperature (37° C.) and low temperature (5° C.), for 6 months respectively, while its characteristics, flavor, taste, sensory properties, saponin components, *E. coli* count, viable bacterial cell count, and the like were tested. The results confirmed that the red ginseng prepared according to the method of present invention was stable in all the test items for quality stability (data not shown).

The method for preparing red ginseng according to the present invention has an advantage in that it allows red ginseng having useful components and superior efficacy to be produced at large amounts within a shorter time period than that of the conventional method for preparing red ginseng. Although the red ginseng or red ginseng powder prepared according to the method of present invention may be used intact, it is preferred that the red ginseng and red ginseng powder are used directly as a raw material of secondary processed red ginseng products, because they need not to be subjected to an additional powdering process as they have a size similar to that of a rice grain or are in the form of powder. Examples of the secondary processed red ginseng products include, but are not limited to, red ginseng capsules, red ginseng tablets, red ginseng extracts, red ginseng tinctures, red ginseng elixirs, red ginseng syrups, red ginseng electuaries and red ginseng tea.

In another aspect, the present invention provides a method for preparing puffed food enriched with red ginseng, from raw ginseng.

Hereinafter, the method for preparing the puffed food enriched with red ginseng according to the present invention will be described.

Step 1: Mixing of Raw Ginseng with Grain Powder and Pre-drying

In order to prepare puffed food enriched with red ginseng according to the present invention, raw ginseng and grain power are mixed with each other and dried.

For puffing in an extrusion process, starch-containing grain powder is mixed with raw ginseng. Examples of the grain powder may be selected from the group consisting of starch, unpolished rice powder, rice powder, wheat powder, corn powder, glutinous rice powder, barley powder and a mixture thereof, but are not limited thereto. The grain powder may be mixed with raw ginseng at the amount of 50–500 parts by weight, preferably 100–300 parts by weight, and more preferably 200 parts by weight, relative to 100 parts by weight of the raw ginseng.

If necessary, emulsifier, soybean protein, calcium enrichment agent, modified starch, calcium propionate or sodium propionate may be added to the mixture in order to improve the quality of puffed food products.

Before mixing, raw ginseng can be washed with water to remove foreign materials and contaminants from its surface and then water remaining on its surface can be removed.

Although raw ginseng itself may be mixed with the grain powder, the raw ginseng is preferably crushed into pieces having the desired size, particularly a size similar to that of a rice grain, in order to shorten the drying time.

For the easy feeding into an extruder, the easy movement in the extruder and the generation of mechanical energy by friction, the moisture content of the mixture needs to be adjusted to less than 40 wt % and preferably 5–40 wt %.

It will be obvious to a person skilled in the art that if white ginseng generally having a moisture content of less than 14 wt % and prepared by the drying of raw ginseng, is mixed with the gain powder, it can be used in the method of present invention without passing through the pre-drying step.

A drying method which can be used in this pre-drying step includes, but is not limited to, ambient temperature drying, hot air drying and freeze drying. The hot air drying method is preferred.

Step 2: Extrusion

The mixture of raw ginseng and grain powder from said mixing and drying steps is fed into an extruder and extruded in the extruder.

If the raw ginseng has been crushed before the mixing step, the mixture itself may be fed into the extruder. In the case of white ginseng and the raw ginseng having been dried without crushing, they are preferably crushed before being fed into the extruder.

The extruder used in the present invention is not limited to products of certain manufacturers. The extruder used in this extrusion step may be a product having the same construction as that of the extruder used in the above-described method for preparing the red ginseng. However, for puffing, this extrusion step should be performed with injecting compressed gas. The compressed gas is preferably injected at a pressure of 0.1–10 MPa, particularly 0.2 MPa. The compressed gas is preferably $CO_2$, $N_2$, compressed air or critical carbonic acid, particularly $CO_2$.

This extrusion step is preferably performed at a dried mixture-feeding rate of 80–150 g/ml, a die exit temperature of 70–180° C., and a screw rotational speed of 100–400 rpm.

It was confirmed that if the die exit temperature is adjusted to a temperature range of 105–180° C., a directly puffed snack is then prepared, and if the die exit temperature is adjusted to a temperature range of 70–105° C., an indirectly puffed pellet is then prepared.

Step 3: Drying and Cutting of Extrudate

For the improvement in storage stability, it is preferred that the puffed extrudate prepared in said extrusion step is additionally dried to a moisture content of less than 10 wt %. A drying method which can be used for drying the puffed extrudate in this step includes, but is not limited to, ambient temperature drying, hot air drying and freeze drying. The hot air drying at less than 100° C., particularly 80° C., is preferred.

The puffed extrudate may be cut into easy-to-eat pieces. Also, the surface of the puffed extrudate may be coated with spices, such as chocolate, banana, cheese and pizza perfumes according to preferences.

By the above method, puffed foods containing a high concentration of red ginseng is provided. The puffed foods include a directly puffed snack that is a ready-to-eat food, as well as a popcorn-type, indirectly puffed pellet, which can be easily popped in a microwave or oven before eating. Since the puffed foods of present invention contain a high concentration of red ginseng, they can be used for light meals and cocktail appetizers while providing a health promotion effect.

BRIEF DESCRIPTION OF THE DRAWINGS

FIG. 3 is a photography showing the results of TLC chromatography for red ginseng prepared according to the method of present invention, white ginseng, the conventional red ginseng and maltol reference standard.

EXAMPLES

Hereinafter, the present invention will be described in further detail by examples. However, it will be obvious to a person skilled in the art that the present invention is not limited to or by the examples.

Test Example 1

Analysis of Characteristics of Raw Ginseng According to Change in Pre-drying Temperature In order to optimize a drying method and temperature for use in the pre-drying step of the red ginseng preparation method according to the present invention, the moisture content, component content and chromaticity of raw ginseng according to changes in the drying method and temperature were measured.

1-1: Analysis of Moisture Content of Raw Ginseng

Figure 1:
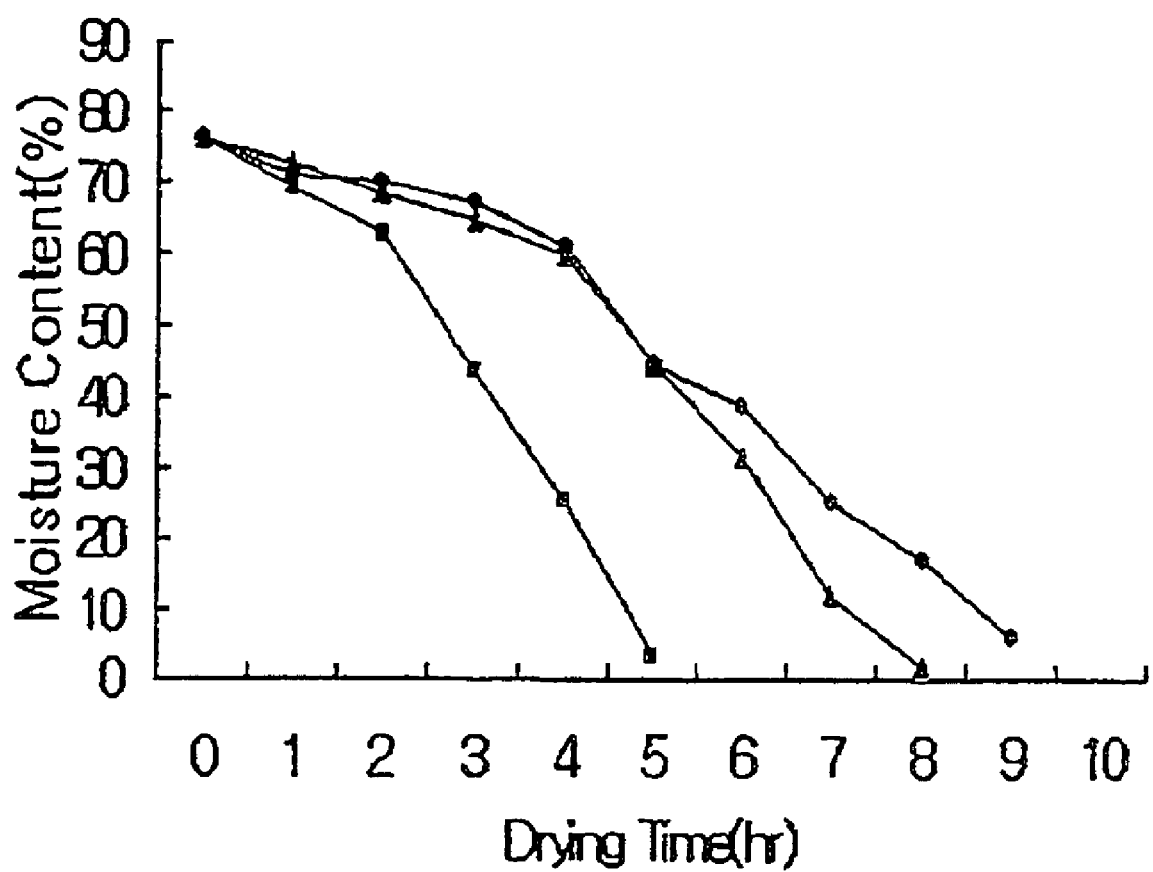
FIG. 1 is a graphic diagram showing the moisture content of raw ginseng according to changes in drying temperature and time (●: 80° C.; ▲: 100° C.; and ■: 120° C.).

Raw ginseng (Koryoinsamteo Co., Korea) was washed four times with water to remove foreign material from its surface, and then water remaining on its surface was removed. The raw ginseng was crushed into pieces having a size similar to that of a rice grain, using a vegetable cutter (Wha Jin Precision Co., Korea). One group of the crushed raw ginseng samples was freeze-dried, and another group of the samples was hot air-dried in a hot air drier (SM-60, Jongro Instrument Inc., Korea) at varying temperatures of 80° C., 100° C. and 120° C. During the drying procedure, each sample was taken at one-hour intervals and measured for its moisture content using an automatic moisture meter. The average of three measurements is shown in FIG. 1.

1-2: Analysis of Ginsenoside Components of Raw Ginseng

The analysis of ginsenoside content was performed for the hot air-dried raw ginseng samples at each temperature and the freeze-dried raw ginseng sample, and each sample had a moisture content of 8 wt %.

First, the separation and quantitative analysis of crude saponin were performed by water-saturated butanol extraction (Namba et al., *Yakugaku Zasshi* 94(2): 252–260, 1974). That is, 3 g of the raw ginseng sample was added to 50 ml of 80% methanol, and the solution was extracted four times at 75° C. for one hour each time, and centrifuged at 4° C. and 8,000 rpm for 30 minutes, and then the supernatant was concentrated under reduced pressure at 50° C. or below. The concentrate was dissolved in 50 ml of distilled water, and 50 ml of ether was added to the resulting solution and shaken, and then, fat-soluble materials that have been moved to the ether layer were removed. 50 ml of water-saturated n-butanol was added to the aqueous layer, and the solution was extracted three times, and washed two times with each 50 ml of distilled water. Then, the extract was concentrated under reduced pressure at 55° C. and dried at 105° C. for 2 hours, thus isolating crude saponin.

Then, the isolated crude saponin was dissolved in methanol, filtered through a 0.45-μm milipore filter and analyzed using HPLC (ALC-224) under the conditions given in Table 1 below. The contents of ginsenosides $R_{b1}$, $R_{b2}$, $R_c$, $R_d$, $R_e$, $R_f$, $R_{g2}$ and $R_{g1}$ were calculated by comparing peak areas on HPLC chromatograms with a calibration curve. The results are given in Table 2 below.

TABLE 1

| | Conditions |
|---|---|
| Column | Lichrosorb $NH_2$ (Merck Co., 10 μm, 4 mm ID × 250 mm) |
| Mobile phase | Acetonitrile/distilled water/n-butanol (70%:20%:10%) |
| Elution rate | 1.0 ml/min |
| Chart rate | 0.5 cm/min |
| Detector | RI-401(differential refractometer) |

1-3: Analysis of Chromaticity of Raw Ginseng

The chromaticity of ginsenosides was analyzed for the hot air dried raw ginseng samples at each temperature and the freeze-dried raw ginseng sample, and each sample had a moisture content of 8 wt %.

Each of the dried raw ginseng samples was measured for its brightness, redness and yellowness using a chromameter (Minolta, CR-200). The measured results were substituted into the following equation to calculate total color difference ($\Delta E$): $\Delta E = [(L-L^*)+(a-a)+(b-b^*)]^{1/2}$. In the above calculation, the standard value $L^*$ was 97.67, $a^*$ was −0.57 and $b^*$ was 2.70. The results are given in Table 2 below.

TABLE 2

| Drying Temp. (° C.) | Ginsenosides | | | | | | | Chromaticity | | | Total color difference |
|---|---|---|---|---|---|---|---|---|---|---|---|
| | $R_{b1}$ | $R_{b2}$ | $R_c$ | $R_d$ | $R_e$ | $R_{g1}$ | Total | Brightness | Redness | Yellowness | |
| 80 | 0.275 | 0.294 | 0.470 | 0.087 | 0.418 | 0.328 | 1.872 | 65.90 | 2.75 | 20.13 | 31.53 |
| 100 | 0.296 | 0.306 | 0.559 | 0.106 | 0.395 | 0.368 | 2.027 | 59.83 | 5.20 | 20.77 | 37.15 |
| 120 | 0.301 | 0.324 | 0.502 | 0.135 | 0.446 | 0.337 | 2.050 | 56.58 | 7.23 | 20.87 | 40.06 |
| FDRG* | 0.194 | 0.185 | 0.501 | 0.054 | 0.387 | 0.275 | 1.603 | — | — | — | — |

*FDRG: Freeze-dried raw ginseng

As can be seen in Table 2, the content of ginsenosides was higher in the hot air-dried raw ginseng sample than in the freeze-dried raw ginseng sample, and was higher at a drying temperature range of 100–120° C. Such results suggest that the pre-drying step in the method for preparing red ginseng is preferably performed by hot air drying.

Example 1

Preparation of Red Ginseng According to the Present Invention 1-1: Pre-drying of Raw Ginseng Raw ginseng (Koryoinsamteo Co., Korea) was washed four times with water to remove foreign materials and then water remaining on its surface was removed. The raw ginseng was crushed into pieces having a size similar with that of a rice grain using a vegetable cutter (Wha Jin Precision Co., Korea). The moisture content of the crushed raw ginseng was 76.3 wt % as measured by an automatic moisture meter (MB200, Ohaus Co. USA). The crushed raw ginseng was dried in a hot air drier (SM-60, Jongro Instrument Inc. Korea) at 100° C. for 6.5 hours, and the dried raw ginseng had a measured moisture content of 29 wt %.

1-2: Extrusion

Figure 2:
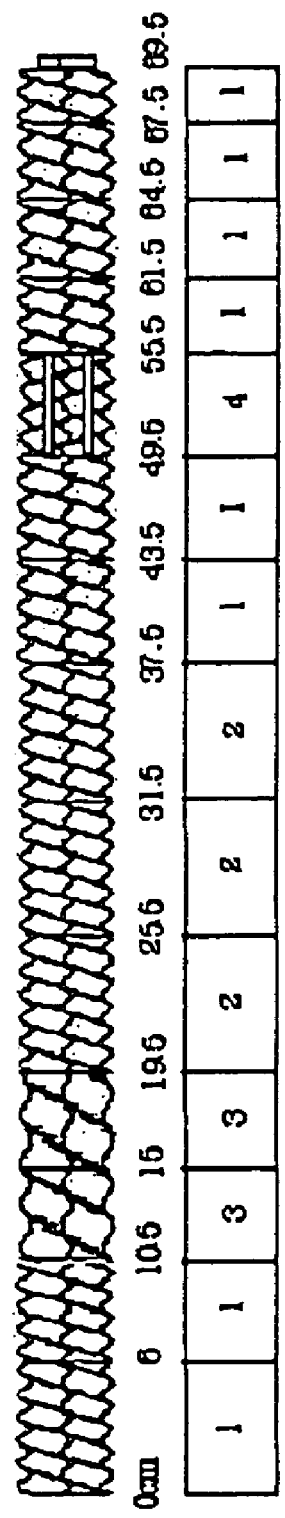
FIG. 2 schematically shows the screw configuration of a twin-screw extruder used in Examples of the present invention (Reference numeral 1: a ½-pitch screw; Reference numeral 2: a ⅔-pitch screw; Reference numeral 3: a forward paddle; Reference numeral 4: a reverse pitch screw).

The raw ginseng having been dried in Example 1-1 was fed into a twin-screw extruder (THK 31, Baeksang Mechanical Co, Korea) and extruded in the extruder to obtain an extrudate. The screw configuration of the twin-screw extruder in this Example is shown in FIG. 2. That is, the screw length-to-diameter (L/D) ratio of the twin-screw extruder was 25:1, a reverse pitch screw was distributed at a location of L/D 13 in order to increase residual time and shear force, and the diameter of a circular die exit was 2.0 mm. The extrusion was performed at a dried raw ginseng-feeding rate of 150 g/min, a die exit temperature of 130° C. and a screw rotational speed of 200 rpm.

1-3: Drying and Grinding of Extrudate

The extrudate prepared in Example 1-2 was dried in a hot air drier (SM-60, Jongro Instrument Inc. Korea) at 100° C. for 15 minutes to reduce its moisture content to 13 wt %. Next, the dried extrudate was powdered in a grinder (Aperture 500 μm, No 35, CHUNG GYE SANG SA).

Examples 2 to 14

Preparation of Red Ginseng According to the Present Invention

Red ginseng products according to the present invention were prepared in the same manner as in Example 1 except that the moisture content of dried raw ginseng, die exit temperature and screw rotational speed were changed. The moisture content of dried raw ginseng, die exit temperature and screw rotational speed in each of Examples 1 to 14, are given in Table 3 below.

TABLE 3

| Example No. | Drying temperature (° C.) | Moisture content of raw ginseng (wt %) | Die exit temperature (° C.) | Screw rotational speed (rpm) |
|---|---|---|---|---|
| 1 | 100 | 29 | 130 | 200 |
| 2 | 100 | 22 | 130 | 250 |
| 3 | 100 | 22 | 130 | 150 |
| 4 | 100 | 15 | 130 | 200 |
| 5 | 100 | 29 | 110 | 150 |
| 6 | 100 | 22 | 110 | 200 |
| 7 | 100 | 15 | 110 | 200 |
| 8 | 100 | 15 | 110 | 150 |
| 9 | 100 | 29 | 90 | 200 |
| 10 | 100 | 22 | 90 | 250 |
| 11 | 100 | 22 | 90 | 150 |
| 12 | 100 | 15 | 90 | 200 |
| 13 | 100 | 22 | 110 | 200 |
| 14 | 100 | 22 | 110 | 200 |

Example 15

Preparation of Indirectly Puffed Pellet Enriched with Red Ginseng According to the Present Invention 15-1: Mixture of Raw Ginseng and Unpolished Rice Powder and Pre-drying of the Mixture Raw ginseng (Koryoinsamteo Co., Korea) was washed four times with water to remove foreign materials, and then water remaining on its surface was removed. The raw ginseng was crushed into pieces having a size similar to that of a rice grain, using a vegetable cutter (Wha Jin Precision Co., Korea). 200 g of the crushed raw ginseng was mixed with 400 g of unpolished rice powder. The mixture was dried in a hot air drier (SM-60, Jongro Instrument Inc., Korea) at 100° C. for 6.5 hours. The dried mixture had a measured moisture content of 30 wt %.

15-2: Extrusion

The mixture of raw ginseng and unpolished rice powder having been dried in Example 15-1 was extruded in a twin-screw extruder (THK31, Baeksang Mechanical Co., Korea) to obtain an extrudate. Although the extruder in Example 1-2 was used, the extrusion was performed with the injection of $CO_2$ for the puffing of the raw material. In order to perform the injection of $CO_2$ gas, a $CO_2$ injection system was disposed at the 67.5 cm location of a screw. The injection system was consisting of a cooler for liquefying $CO_2$ gas; a compressor for pressurizing the liquefied $CO_2$ gas above 73 bar; and a heater for heating the compressed $CO_2$ above 31° C. In addition, in order to prevent $CO_2$ from flowing backward toward a raw material feeding portion, a ½ pitch screw just before the $CO_2$ injection portion was replaced by a reverse pitch screw. During the extrusion, $CO_2$ gas was injected at a pressure of 0.2 MPa using the $CO_2$ gas injection system. The extrusion was performed at a dried mixture-feeding rate of 100 g/min, a die exit temperature of 80° C. and a screw rotational speed of 200 rpm.

15-3: Drying and Cutting of Extrudate

The indirectly puffed extrudate prepared in Example 14-2 above was dried in a hot air drier (SM-60, Jongro Instrument Inc., Korea) at 80° C. for 15 minutes to reduce its moisture content to 8 wt %. Then, the dried puffed extrudate was cut into pieces having a size of 8 cm. The cut puffed extrudate pieces were coated with chocolate.

Example 16

Preparation of Directly Puffed Snack Enriched with Red Ginseng According to the Present Invention A directly puffed snack enriched with red ginseng according to the present invention was prepared in the same manner as in Example 15 except that a die exit temperature of 110° C. other than 80° C. was used in the extrusion step.

Test Example 2

Component Analysis of Red Ginseng According to the Present Invention

The components of the red ginseng having been prepared in Examples 1 to 14 above were compared with those of the commercially available conventional red ginseng (control group). The conventional red ginseng used in this Example was purchased from Korea Ginseng Corp., Korea.

2-1: Content Analysis of Saponin Component

The ginsenoside contents of the red ginseng having been prepared in Examples 1 to 14 above were analyzed by the method described in Test Example 1–2 above.

The ginsenoside contents measured as such are given in Table 4 below. As can be seen in Table 4, the red ginseng according to the present invention had higher ginsenoside total contents than that of the conventional red ginseng.

TABLE 5

| Example No. | Reducing sugar (wt %) | Total sugar (wt %) | Acidic polysaccharides (wt %) |
|---|---|---|---|
| 1 | 15.10 | 47.77 | 3.39 |
| 2 | 18.19 | 48.68 | 2.94 |
| 3 | 17.16 | 48.43 | 2.82 |
| 4 | 16.85 | 44.47 | 3.19 |
| 5 | 18.43 | 45.44 | 3.08 |
| 6 | 18.03 | 46.17 | 2.44 |
| 7 | 19.29 | 48.77 | 3.20 |
| 8 | 19.22 | 47.90 | 2.98 |
| 9 | 18.45 | 45.71 | 3.02 |
| 10 | 18.28 | 45.38 | 2.88 |
| 11 | 16.89 | 45.29 | 3.20 |
| 12 | 16.81 | 45.07 | 2.72 |
| 13 | 18.03 | 46.17 | 2.44 |
| 14 | 18.03 | 46.17 | 2.44 |
| Control | 14.31 | 45.88 | 7.24 |

TABLE 4

| Example No. | $R_{g1}$ | $R_{g2}$ | $R_{g3}$ | $R_f$ | $R_e$ | $R_d$ | $R_c$ | $R_{b1}$ | $R_{b2}$ | $Y_{PD/PT}$ | (mg/g) Total |
|---|---|---|---|---|---|---|---|---|---|---|---|
| 1 | 1.921 | 1.007 | 0.156 | 0.957 | 4.376 | 1.687 | 2.822 | 4.532 | 1.949 | 1.306 | 19.406 |
| 2 | 2.070 | 1.065 | — | 1.095 | 4.637 | 1.904 | 3.027 | 4.753 | 2.036 | 1.322 | 20.588 |
| 3 | 2.121 | 1.044 | — | 1.122 | 4.724 | 2.010 | 3.074 | 4.884 | 2.107 | 1.340 | 21.087 |
| 4 | 2.117 | 1.084 | 0.178 | 1.190 | 4.682 | 2.018 | 3.324 | 4.953 | 2.131 | 1.343 | 21.673 |
| 5 | 2.138 | 0.992 | — | 1.231 | 4.928 | 2.051 | 3.133 | 4.910 | 2.109 | 1.314 | 21.492 |
| 6 | 2.263 | 1.179 | — | 1.311 | 4.885 | 2.116 | 3.367 | 4.842 | 2.159 | 1.295 | 22.122 |
| 7 | 2.365 | 1.232 | | 1.243 | 4.865 | 1.921 | 3.240 | 4.746 | 2.071 | 1.234 | 21.681 |
| 8 | 2.269 | 0.755 | — | 1.171 | 4.295 | 1.824 | 3.100 | 1.359 | 1.880 | 0.961 | 16.652 |
| 9 | 2.166 | 0.704 | — | 1.044 | 3.916 | 1.001 | 2.519 | 3.892 | 1.618 | 1.153 | 16.859 |
| 10 | 2.360 | 0.768 | — | 1.260 | 4.849 | 1.813 | 3.115 | 4.771 | 1.975 | 1.264 | 20.912 |
| 11 | 2.347 | 0.744 | — | 1.202 | 4.323 | 1.471 | 2.643 | 4.143 | 1.682 | 1.154 | 18.555 |
| 12 | 2.150 | 0.665 | 0.132 | 1.229 | 4.453 | 1.680 | 2.870 | 4.589 | 1.911 | 1.281 | 19.678 |
| 13 | 2.263 | 1.179 | — | 1.311 | 4.885 | 2.116 | 2.905 | 4.842 | 2.159 | 1.295 | 22.122 |
| 14 | 2.263 | 1.179 | — | 1.311 | 4.885 | 2.116 | 2.905 | 4.842 | 2.159 | 1.295 | 22.122 |
| Control | 2.446 | 1.451 | 0.371 | 1.143 | 2.333 | 0.422 | 1.902 | 4.801 | 1.507 | 1.173 | 16.376 |

$Y_{PD/PT}$ represents the weight ratio of protopanaxadiol ginsenoside (PD) including $R_{b1}$, $R_{b2}$, $R_c$ and $R_d$ to protopanaxatriol ginsenoside (PT) including $R_e$, $R_f$, $R_{g3}$, $R_{g2}$ and $R_{g1}$.

2-2: Content Analysis of Non-saponin Component

The contents of total sugar and reducing sugar were analyzed by the dinitrosalicylic acid (DNS) method (Colowick, S. P. and Kaplem, N. O., *Methods in enzymology* 1: 149, 1955). The content analysis of acidic polysaccharides was performed by the carbazole-sulfuric acid method (Jae-Ho Do et al., the *Korean Society of Ginseng* 17: 139–144, 1993). That is, 0.1 wt % ethanol as a substitute for carbozole was used in the blank, and 0.5 ml of the sample was mixed with 3 ml of c-$H_2SO_4$, heated in a water bath at 85° C. for 5 minutes and then measured for absorbance at 525 nm.

The contents of non-saponin components, which had been measured by the above method, are given in Table 5 below. As can be seen in Table 5, the red ginseng according to the present invention had higher total sugar and reducing sugar contents and lower acidic polysaccharide contents than those of the conventional red ginseng.

2-3: Confirmation of Presence of Maltol

In order to confirm the production of maltol having antioxidant activity, which is a characteristic component of red ginseng and is found only in red ginseng but not in raw ginseng, TLC chromatography was performed for the red ginseng of Examples 1 to 12, maltol reference standard, white ginseng and the conventional red ginseng. That is, 100 ml of 80% methanol was added to 5 g of each sample, and the solution was extracted two times at 70° C. for one hour each time and filtered through filter paper (Whatman No. 41). The filtrate was collected, to which 50 ml of distilled water and 50 ml of ethyl acetate were then added. The mixture was shaken, and the upper layer was separated and concentrated under reduced pressure at 40° C. 1 ml of HPLC methanol was added to the concentrate in a flask to dissolve the concentrate, and analyzed in a vial. 5 mg of maltol reference standard was dissolved in 1 ml of methanol and used as a standard solution. 5–10 μl of each of the assay solution and the standard solution was dropped on a thin film chromatography silica gel plate, and then the thin film plate that had been developed about 10 cm by hexane-acetic acid (4:1, v/v) as a developing solvent was dried. Ferric chloride ($FeCl_3$) solution was uniformly sprayed on the dried plate and dried at 110° C. for 5 minutes. Then, one spot of several spots detected in the assay solution was made equal to the color and $R_f$ value of a red-violet spot detected in the standard solution, and heated at 110° C. for 5 minutes and then analyzed.

The analysis results are shown in FIG. 3. As can be seen in FIG. 3, maltol, a characteristic component of red ginseng, was detected in all the red ginseng products having been prepared in Examples 1 to 12. This suggests that red ginseng is prepared by the method for preparing red ginseng according to the present invention.

Test Example 3

Analysis of Chromaticity of Red Ginseng According to the Present Invention

The chromaticity of the red ginseng products having been prepared in Examples 1 to 14 above was compared with that of the commercially available conventional red ginseng (control group). The conventional red ginseng was purchased from Korean Ginseng Corp., Korea.

3 g of each red ginseng sample was dispersed in 200 ml of distilled water, and the dispersion was extracted in water bath at 80° C. for 3 hours and cooled at 20° C. The cooled extract was filtered through filter paper (Whatman No. 41) and centrifuged at 8,000 rpm for 20 minutes. The supernatant was measured for absorbance at 440 nm using a spectrometer (TU-1800, Human Co. USA), thus determining brownness. The brightness, yellowness, redness and total color difference of the red ginseng samples were measured in the same manner as in Test Example 1–3 above.

The chromaticity measurement results obtained in the above procedure are given in Table 6. As can be seen in Table 6, the chromaticity of the red ginseng having been prepared according to the present invention is almost similar to that of the conventional red ginseng.

TABLE 6

| Example No. | Brownness | Brightness | Yellowness | Redness | Total color difference |
|---|---|---|---|---|---|
| 1 | 0.872 | 55.33 | 4.47 | 21.26 | 51.21 |
| 2 | 0.769 | 56.80 | 4.45 | 22.46 | 50.38 |
| 3 | 0.880 | 59.48 | 4.40 | 23.18 | 48.50 |
| 4 | 1.323 | 56.51 | 5.63 | 24.67 | 51.58 |
| 5 | 0.784 | 61.28 | 4.80 | 23.26 | 47.02 |
| 6 | 0.909 | 61.90 | 4.53 | 21.10 | 46.42 |
| 7 | 1.117 | 61.26 | 4.82 | 23.52 | 47.18 |
| 8 | 1.496 | 60.90 | 5.16 | 23.65 | 47.50 |
| 9 | 0.943 | 62.54 | 4.94 | 24.43 | 46.48 |
| 10 | 0.893 | 62.97 | 4.43 | 23.25 | 45.58 |
| 11 | 0.876 | 61.09 | 4.88 | 24.29 | 47.57 |
| 12 | 1.419 | 57.74 | 5.62 | 24.33 | 50.43 |
| 13 | 0.909 | 61.90 | 4.53 | 23.10 | 46.42 |
| 14 | 0.909 | 61.90 | 4.53 | 23.10 | 46.42 |
| Control | 1.660 | 60.42 | 6.86 | 25.16 | 48.75 |

INDUSTRIAL APPLICABILITY

As described above, the red ginseng and red ginseng powder prepared according to the method of present invention can be produced at larger amounts within a shorter time period than those of the conventional method for preparing red ginseng. In addition, since the red ginseng and red ginseng powder of the present invention need not to be subjected to an additional powdering step, they may be directly used as a raw material of secondary processed red ginseng products. Furthermore, as the directly puffed snack and indirectly puffed pellet prepared according to the method of present invention contain a high concentration of red ginseng, they may be used for light meals and cocktail appetizers while providing a health promotion effect.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention of the appended claims.

What is claimed is:

1. A method for preparing extruded red ginseng, which comprises the steps of:
    drying raw ginseng to reduce the moisture content of the raw ginseng to a range of 5–40% wt; and
    extruding the dried raw ginseng in an extruder comprising a die exit and a screw having a screw rotational speed, wherein the die exit temperature of the extruder is 70–150° C., and the screw rotational speed of the extruder is 100–400 rpm.

2. The method of claim 1, which additionally comprises the step of crushing the raw ginseng into pieces prior to the drying step.

3. A method for preparing puffed food enriched with extruded red ginseng, which comprises the steps of:
    mixing raw ginseng with grain powder;
    drying the mixture to reduce the moisture content of the mixture to a range of 5–40% wt; and
    extruding the dried mixture in an extruder with injecting compressed gas, comprising a die exit and a screw having a screw rotational speed, wherein the die exit temperature of the extruder is 70–180° C., and the screw rotational speed of the extruder is 100–400 rpm.

4. The method of claim 3, wherein the grain powder is selected from the group consisting of unpolished rice powder, rice powder, wheat powder, corn powder, glutinous rice powder, barley powder and a mixture thereof.

5. The method of claim 3, which additionally comprises the step of crushing the raw ginseng into pieces prior to the drying step.

6. The method of claim 3, wherein the injection of the compressed gas is performed by injecting $CO_2$ at 0.1–10 MPa.

7. The method of claim 3, which additionally comprises the steps of drying and cutting the extrudate.

8. The method of claim 3, wherein the extruding step is performed at a die exit temperature of 105–180° C., and the puffed food is a directly puffed snack.

9. The method of claim 3, wherein the extruding step is performed at a die exit temperature of 70–105° C., and the puffed food is an indirectly puffed pellet.

* * * * *